(12) United States Patent
Di Marzo et al.

(10) Patent No.: US 10,226,433 B2
(45) Date of Patent: Mar. 12, 2019

(54) USE OF CANNABINOIDS IN THE TREATMENT OF DEGENERATIVE SKELETAL MUSCLE DISEASES

(71) Applicant: GW Research Limited, Histon, Cambridge, Cambridgeshire (GB)

(72) Inventors: Vincenzo Di Marzo, Cambridge (GB); Colin Stott, Cambridge (GB); Keith Foster, Reading (GB); Fabio Iannotti, Pozzuoli (IT)

(73) Assignee: GW Research Limited, Histon, Cambridge, Cambridgeshire (GB)

( * ) Notice: Subject to any disclaimer, the term of this patent is extended or adjusted under 35 U.S.C. 154(b) by 0 days.

(21) Appl. No.: 15/518,297

(22) PCT Filed: Oct. 14, 2015

(86) PCT No.: PCT/GB2015/053044
§ 371 (c)(1),
(2) Date: Apr. 11, 2017

(87) PCT Pub. No.: WO2016/059411
PCT Pub. Date: Apr. 21, 2016

(65) Prior Publication Data
US 2017/0304217 A1   Oct. 26, 2017

(30) Foreign Application Priority Data
Oct. 14, 2014 (GB) .................................. 1418172.1

(51) Int. Cl.
| | |
|---|---|
| *A61K 31/05* | (2006.01) |
| *A61P 21/00* | (2006.01) |
| *A61K 31/352* | (2006.01) |
| *A61K 36/185* | (2006.01) |
| *A61K 45/06* | (2006.01) |
| *A61K 31/015* | (2006.01) |
| *A61K 31/047* | (2006.01) |

(52) U.S. Cl.
CPC ............ *A61K 31/05* (2013.01); *A61K 31/015* (2013.01); *A61K 31/047* (2013.01); *A61K 31/352* (2013.01); *A61K 36/185* (2013.01); *A61K 45/06* (2013.01); *A61K 2300/00* (2013.01)

(58) Field of Classification Search
CPC ..... A61K 31/05; A61K 31/352; A61K 36/185
See application file for complete search history.

(56) References Cited

PUBLICATIONS

Tabebordbar et al. Annu. Rev. Pathol. Mech. Dis. 2013, 8, 441-475.*
GB1418172.1, Jun. 25, 2015, Combined Search and Examination Report under Sections 17 and 18(3).
PCT/GB2015/053044, Feb. 3, 2016, International Search Report and Written Opinion.
PCT/GB2015/053044, Feb. 1, 2017, International Preliminary Report on Patentability.
[No Author Listed] Medical Marijuana and Muscular Dystrophy. 2013. Retrieved from <http://www.marijuanadoctors.com/content/ailments/view/114?ailment=muscular-dystrophy> on Nov. 1, 2016.
[No Author Listed] Testimony of Patrick McClellan; Minnesotans for Compassionate Care. 2013. Retrieved from < https://www.mncares.org/testimony-of-patrick-mcclellan/> on Nov. 1, 2016.
Chiarotti et al., Muscular dystrophy in adult mice chronically treated with cannabinoids at behavioral doses. II—Biochemical findings. Acta Medica Romana. 1975;13(6):423-46.
Cooper, A new role for ion channels in myoblast fusion. J Cell Biol. May 14, 2001;153(4):F9-12.
Giusti et al., Muscular dystrophy in mice after treatment with cannabinoids. Acta Medica Romana. 1978;15(4/5):339-48.
Giusti et al., Muscular dystrophy in mice after chronic subcutaneous treatment with cannabinoids. Forensic Sci. Sep.-Oct. 1977;10(2):133-40.
Hill et al., Cannabidivarin-rich cannabis extracts are anticonvulsant in mouse and rat via a CB1 receptor-independent mechanism. Br J Pharmacol. Oct. 2013;170(3):679-92. doi:10.1111/bph.12321.
Hill et al., Phytocannabinoids as novel therapeutic agents in CNS disorders. Pharmacol Ther. Jan. 2012;133(1):79-97. doi: 10.1016/j.pharmthera.2011.09.002. Epub Sep. 6, 2011.
Iannotti et al., Expression, localization, and pharmacological role of Kv7 potassium channels in skeletal muscle proliferation, differentiation, and survival after myotoxic insults. J Pharmacol Exp Ther. Mar. 2010;332(3):811-20. doi:10.1124/jpet.109.162800. Epub Dec. 29, 2009.
Iannotti et al., Specification of skeletal muscle differentiation by repressor element-1 silencing transcription factor (REST)-regulated Kv7.4 potassium channels. Mol Biol Cell. Feb. 2013;24(3):274-84. doi: 10.1091/mbc.E11-12-1044. Epub Dec. 14, 2012.
Passatore et al., Muscular dystrophy in adult mice chronically treated with cannabinoids at behavioral doses. III—Functional tests on muscle. Acta Medica Romana. 1975;13(6):427-31.
Shieh, Muscular dystrophies and ther genetic myopathies. Neurol Clin. Nov. 2013;31(4):1009-29. doi: 10.1016/j.ncl.2013.04.004.

\* cited by examiner

*Primary Examiner* — Irina Neagu
(74) *Attorney, Agent, or Firm* — Wolf, Greenfield & Sacks, P.C.

(57) ABSTRACT

The present invention relates to the use of cannabinoids in the treatment of degenerative skeletal muscle disease. In particular the degenerative skeletal muscle disease is Duchenne muscular dystrophy (DMD). Preferably the cannabinoids are one or more of: Cannabidiol (CBD); Cannabidivarin (CBDV); and Tetrahydrocannabivarin (THCV).

4 Claims, 9 Drawing Sheets

Effect of 1 and 3 μM CBD and CBDV on C2C12 cell differentiation

Effect of a short-term exposure to CBD in C2C12 myoblasts

USE OF CANNABINOIDS IN THE TREATMENT OF DEGENERATIVE SKELETAL MUSCLE DISEASES

RELATED APPLICATION

This application is a national stage filing under 35 U.S.C. § 371 of International Application No. PCT/GB2015/053044, filed Oct. 14, 2015, which was published under PCT Article 21(2) in English, the entire disclosure of which is incorporated by reference herein in its entirety.

The present invention relates to the use of cannabinoids in the treatment of degenerative skeletal muscle disease. In particular the degenerative skeletal muscle disease is Duchenne muscular dystrophy (DMD).

Preferably the cannabinoids are one or more of: Cannabidiol (CBD); Cannabidivarin (CBDV); and Tetrahydrocannabivarin (THCV).

BACKGROUND TO THE INVENTION

Skeletal myogenesis is a tightly regulated process requiring coordinated changes in expression of a large number of genes allowing proliferating myoblasts to differentiate in to myotubes (Shieh, 2013). This process is altered in many different myopathies; among them, Duchenne muscular dystrophy (DMD), where the regenerative capacity of skeletal muscle precursors cells (satellite) is lost. Their decreased ability to differentiate into mature and functional myotubes leads to progressive muscle weakness with chronic degeneration.

Although there are a large number of functions attributed to the endocannabinoid system, very little is known about its function in the skeletal muscle cell regeneration and differentiation. Recently, it was found that the endocannabinoid 2-AG inhibits differentiation of mouse and human myoblasts through a CB1-dependent mechanism (Iannotti et al. 2013).

Skeletal muscle development is a highly controlled, multifactorial process involving the coordinated regulation of a large number of genes that results in proliferating myoblast cells leaving the cell cycle, and subsequently fusing into ordered arrays of large multinucleated myotubes which further differentiate into mature muscle fibres (Iannotti et al. 2010).

Changes in the expression and functional activation of various classes of ion channels seem to be associated with the myoblast to myotube transition (Cooper, 2001).

Mouse C2C12 cells may be used in an experimental model for in vitro skeletal myogenesis, this method can be used to determine the potential effects of compounds on the skeletal muscle cell differentiation process.

A further model using human satellite cells can also be used as an in vitro test to study cell differentiation. Satellite cells are precursors to skeletal muscle cells, able to give rise to differentiated skeletal muscle cells. Upon activation, satellite cells can re-enter the cell cycle to proliferate and differentiate into myoblasts.

A myocyte is the type of cell found in muscle tissue, these are long, tubular cells that develop from myoblasts to form muscles in a process known as myogenesis. There are various specialized forms of myocytes: cardiac, skeletal, and smooth muscle cells, with various properties.

There are several different types of degenerative skeletal muscle diseases of which Duchenne muscular dystrophy (DMD) is by far the most common. Other types of degenerative skeletal muscle disease include: Becker muscular dystrophy (BMD); Congenital muscular dystrophy; Distal muscular dystrophy; Emery-Dreifuss Muscular Dystrophy; Facioscapulohumeral muscular dystrophy (FSHD); Limb-girdle muscular dystrophy (LGMD); Myotonic muscular dystrophy; and Oculopharyngeal muscular dystrophy.

DMD generally affects only boys (with extremely rare exceptions), becoming clinically evident when a child begins walking. By age 10, the child may need braces for walking and by age 12, most patients are unable to walk.

The life span of DMD patients ranges from 15 to 51. In the early 1990s, researchers identified the gene for the protein dystrophin which, when absent, causes DMD. The amount of dystrophin correlates with the severity of the disease (i.e., the less dystrophin present, the more severe the phenotype).

Since the gene is on the X chromosome, this disorder affects primarily males, and females who are carriers have milder symptoms. Sporadic mutations in this gene occur frequently, accounting for a third of cases. The remaining two-thirds of cases are inherited in a recessive pattern.

Dystrophin is part of a complex structure involving several other protein components. The "dystrophin-glycoprotein complex" helps anchor the structural skeleton (cytoskeleton) within the muscle cells, through the outer membrane (sarcolemma) of each cell, to the tissue framework (extracellular matrix) that surrounds each cell. Due to defects in this assembly, contraction of the muscle leads to disruption of the outer membrane of the muscle cells and eventual weakening and wasting of the muscle.

Glucocorticoids, more precisely prednisone and deflazacort, are the main drug treatments for DMD. They have been used for over two decades and are the only medications that have been shown to increase muscular strength.

As glucocorticoids are anti-inflammatory and immunosuppressant long term use of these compounds can result in many damaging side effects. Immunosuppression is a major problem in long term users of glucocorticoids which in turn can mean that a patient's immune system is less functional leaving them prone to serious infections. In addition wound healing requires a certain amount of inflammation and this can be delayed during glucocorticoid therapy.

Glucocorticoids can also raise blood sugar which in turn can diabetes mellitus. Calcium absorption may be suppressed and osteoporosis may result. Muscle atrophy can also occur with long-term glucocorticoid therapy.

In order to treat degenerative skeletal muscle diseases such as DMD it is important for a medication to enable satellite cell differentiation into myoblasts and myoblast differentiation into myotubes. It is known that CB1 activation also stimulates myoblast proliferation and therefore endocannabinoids, depending on "when" and "where" they act, can both inhibit and stimulate muscle formation by affecting cell cycle and plasticity.

Phytocannabinoids may act directly or indirectly at the CB1 receptor to counteract the effects of its activation. The phytocannabinoids may also counteract inflammatory responses such as those that occur in DMD. These inflammatory responses significantly worsen the consequences of impaired muscle differentiation, thus reducing the life expectancy of DMD patients. Additionally the phytocannabinoids may inhibit endocannabinoid inactivation.

It has been found that phytocannabinoids, in particular the phytocannabinoids CBD and CBDV are effective at enabling satellite cell differentiation into myoblasts and myoblast differentiation into myotubes. This was surprising as these compounds are not CB1 active compounds

BRIEF SUMMARY OF THE DISCLOSURE

In accordance with a first aspect of the present invention there is provided one or a combination of the phytocannabinoids Cannabidiol (CBD); Cannabidivarin (CBDV); and Tetrahydrocannabivarin (THCV) for use in the treatment of degenerative skeletal muscle disease.

In one embodiment the phytocannabinoid is CBD.

In a further embodiment the phytocannabinoid is CBDV.

In an alternative embodiment the phytocannabinoid is THCV.

In a further embodiment still the phytocannabinoids are a combination of THCV and CBD and/or CBDV.

Preferably the degenerative skeletal muscle disease is Duchenne muscular dystrophy (DMD).

Preferably the dose of the phytocannabinoids is between 1 and 1000 mg/kg day.

In a further embodiment there is provided a pharmaceutical formulation comprising one or a combination of the phytocannabinoids Cannabidiol (CBD); Cannabidivarin (CBDV); and Tetrahydrocannabivarin (THCV) and one or more excipients.

In accordance with a second aspect of the present invention there is provided a method of treating a patient suffering from Duchenne muscular dystrophy (DMD) comprising administering one or a combination of the phytocannabinoids Cannabidiol (CBD); Cannabidivarin (CBDV); and Tetrahydrocannabivarin (THCV) to the patient in need thereof.

BRIEF DESCRIPTION OF THE DRAWINGS

Embodiments of the invention are further described hereinafter with reference to the accompanying drawings, in which.

Figure 1:
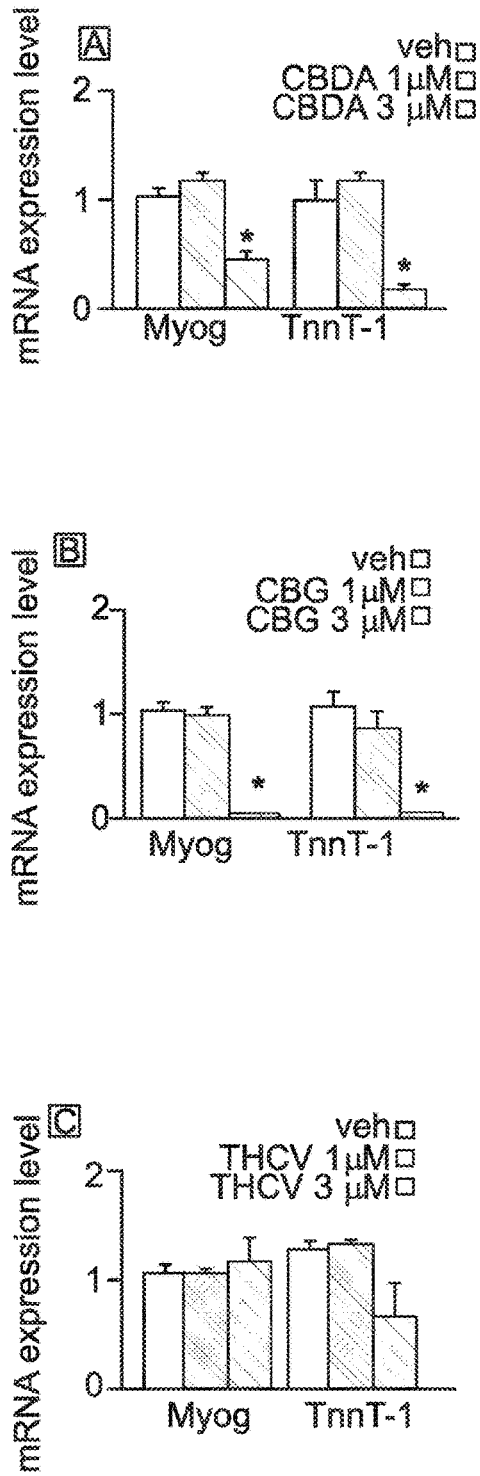
FIG. 1 shows the effect of 1 and 3 µM CBDA, CBG and THCV on C2C12 cell differentiation.

The legends to the figures are described in more details below:

FIG. 1. Myogenin (Myog) and Troponin (Tnnt-1) mRNA expression levels were quantified by qPCR after 24 h of C2C12 cells exposure to DM+CBDA (A), CBG (B) or THCV (C) at the indicated concentrations. Each bar represents the mean±S.E.M. of at least four separate experiments. *p≤0.05 vs. respective vehicle group (white column).

Figure 2:
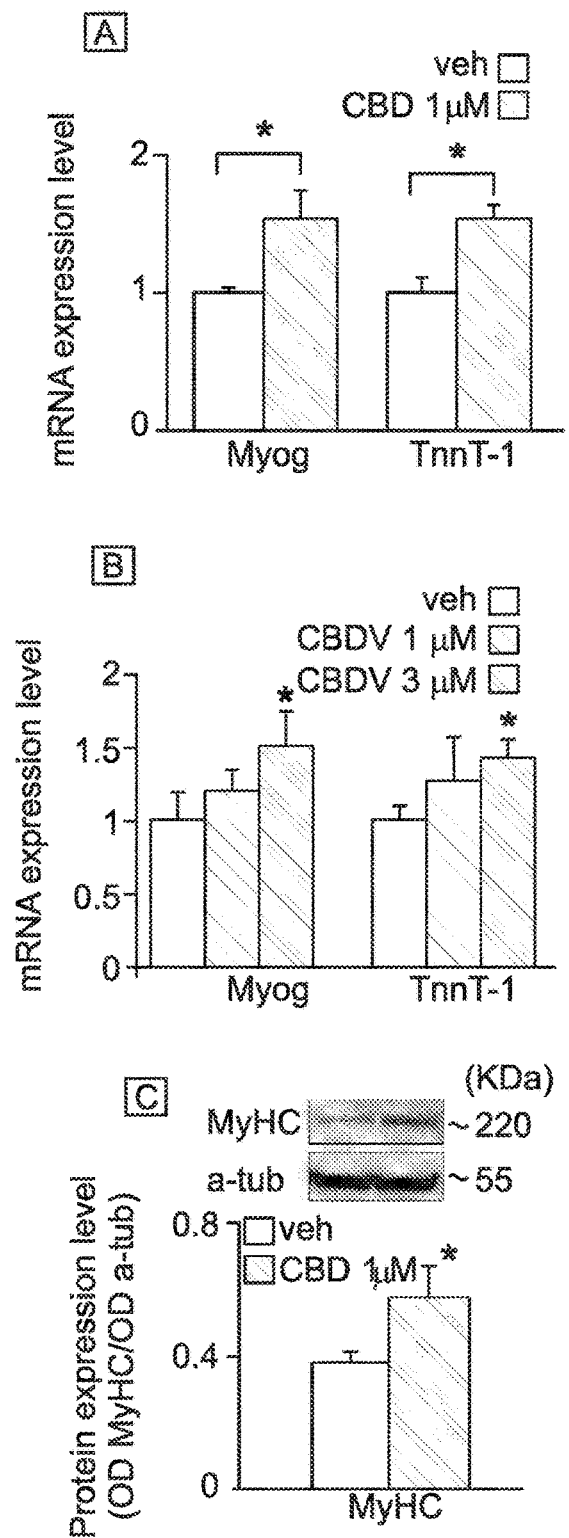
FIG. 2 shows the effect of 1 and 3 µM CBD and CBDV on C2C12 cell differentiation.

FIG. 2. Myogenin (Myog) and Troponin (Tnnt-1) mRNA expression level was quantified by qPCR after 24 h of C2C12 myoblasts exposure to DM+CBD (A) and CBDV (B) at the indicated concentrations. Each bar represents the mean±S.E.M. of at least four separate experiments. *p≤0.05 vs. respective vehicle group (white column). (C) Western blot analysis of MyHC protein levels in differentiating C2C12 cells treated with 1 µM CBD. Representative blots showing the approximate molecular mass of MyHC protein (expressed in KDa) (top) and quantification of the averaged OD values for MyHC normalized to those of α-tubulin (bottom) are shown. *p≤0.05 vs. respective vehicle group (GM). Each data point is from at least four independent determinations.

Figure 3:
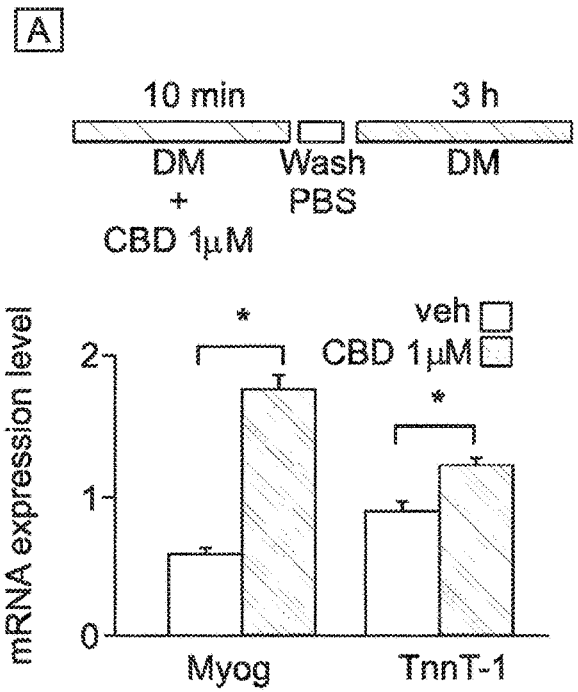
FIG. 3 shows the effect of a short-term exposure to CBD in C2C12 myoblasts.
Figure 3:
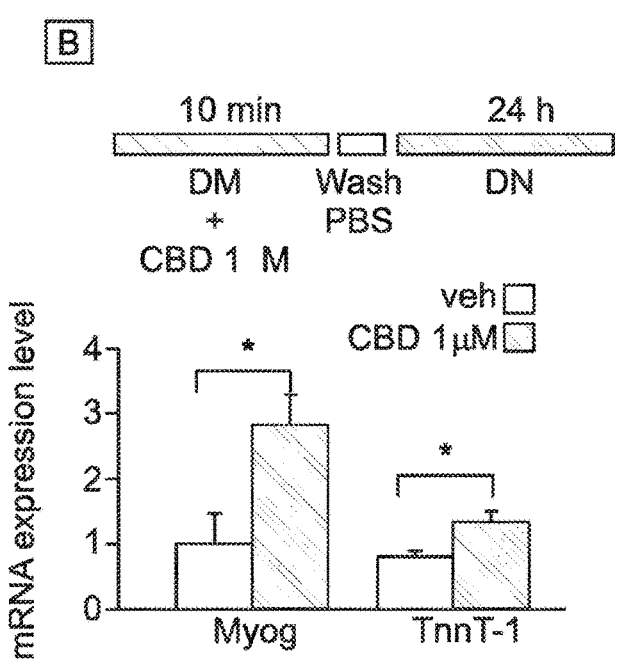

FIG. 3. Myogenin (Myog) and Troponin (Tnnt-1) mRNA expression level was quantified in myoblasts exposed to DM+1 µM CBD for 10 min and then kept in DM without CBD for the subsequent 3 and 24 h.

Figure 4:
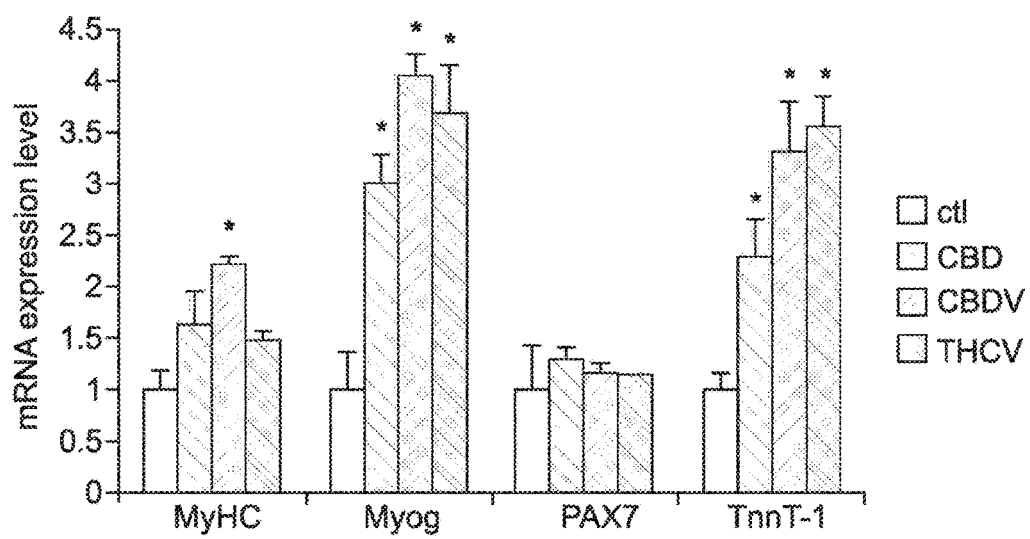
FIG. 4 shows the effect of CBD, CBDV and THCV on satellite cell differentiation.

FIG. 4. Effect of CBD, CBDV and THCV on satellite cell differentiation: Myogenin (Myog), Troponin (Tnnt-1) and Myosin Heavy Chain (MyHC) mRNA expression level was quantified by qPCR after 5 days of SC exposure to DM+CBD (light grey columns), CBDV (dark grey columns) and THCV (white columns). Each bar represents the mean±S.E.M. of at least four separate experiments. *p≤0.05 vs. respective vehicle group (white column).

Figure 5:
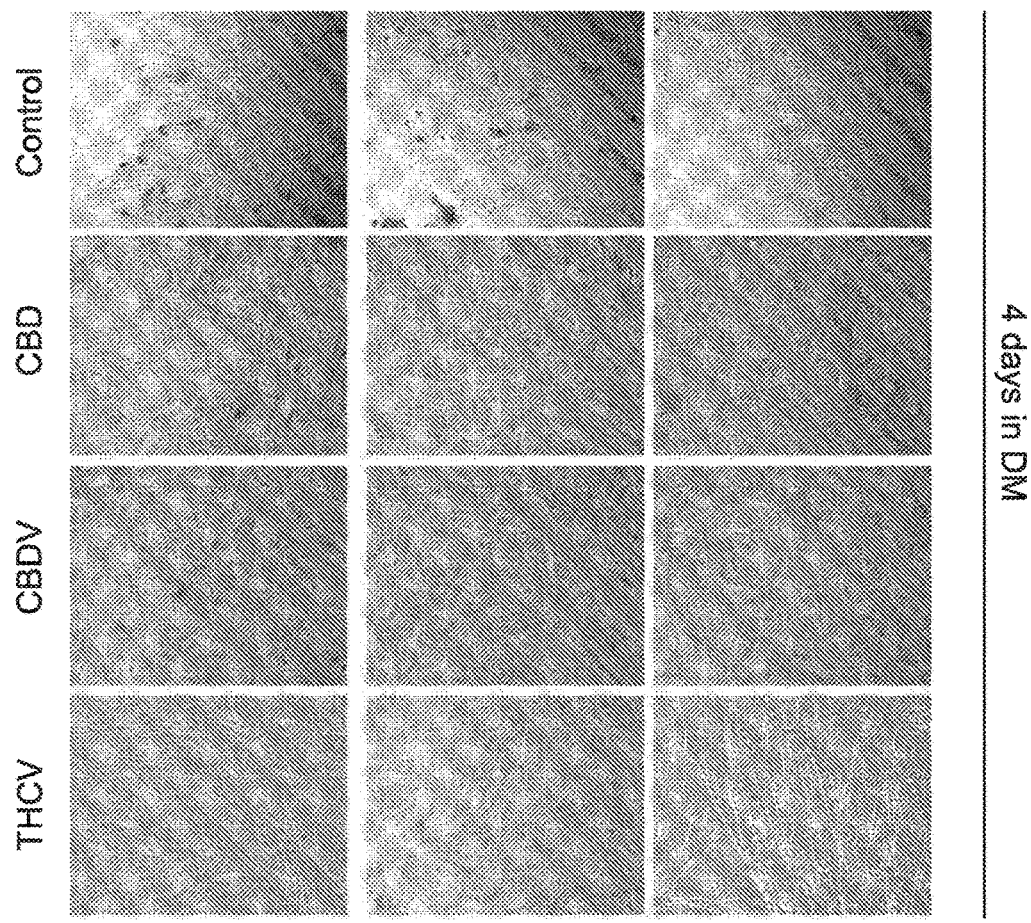
FIG. 5 shows representative phase contrast images of satellite cells treated with CBD, CBDV and THCV at 4 days.

FIG. 5. Representative phase contrast images of satellite cells treated with CBD (1 µM), CBDV and THCV (3 µM) are shown. Images were taken 4 days of cell exposure to DM in presence or not of phytocannabinoid.

Figure 6:
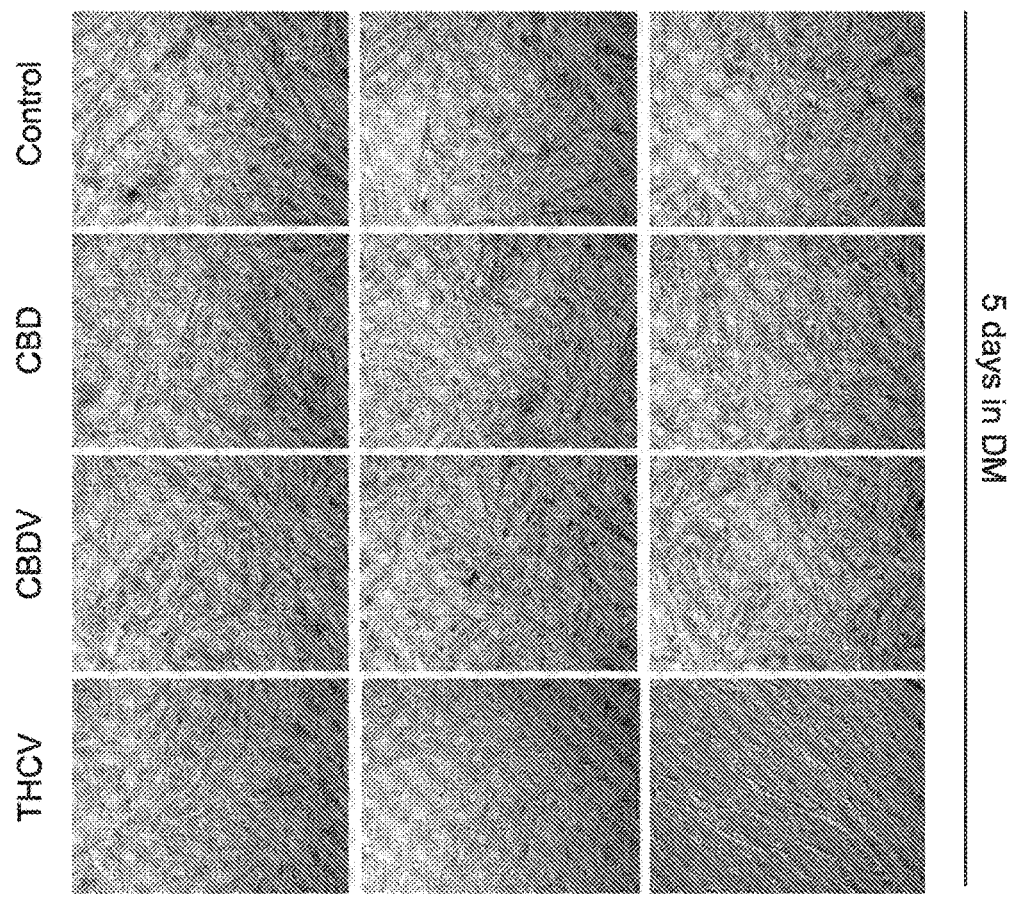
FIG. 6 shows representative phase contrast images of satellite cells treated with CBD, CBDV and THCV at 4 days.

FIG. 6. Representative phase contrast images of satellite cells treated with CBD (1 µM), CBDV and THCV (3 µM) are shown. Images were taken 5 days of cell exposure to DM in presence or not of phytocannabinoid.

Figure 7:
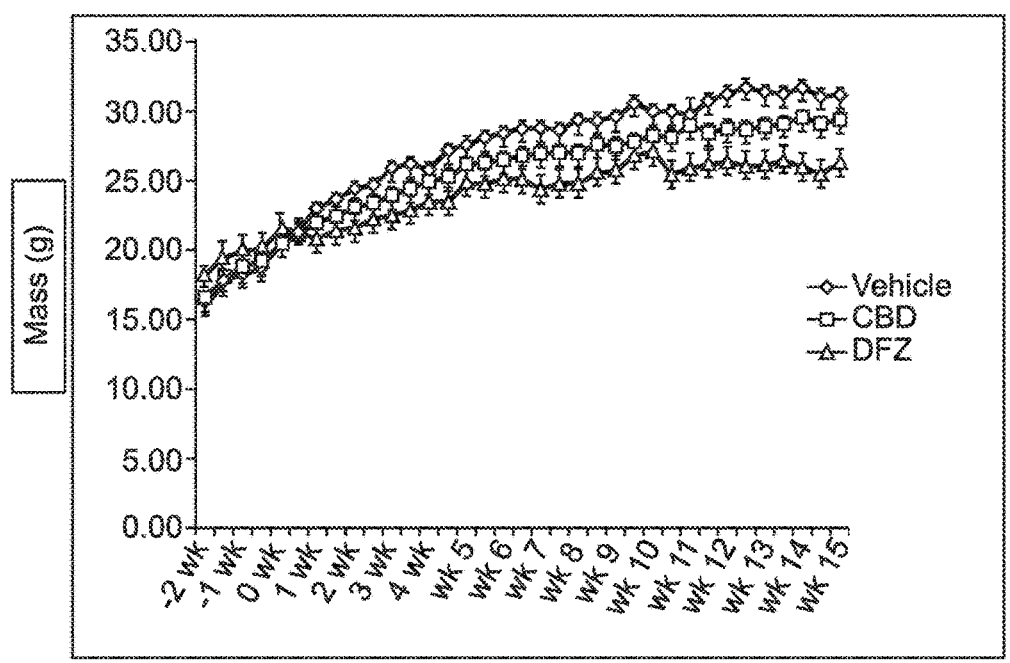
FIG. 7 shows body mass changes in MDX mice after 16 weeks.

FIG. 7 After week 4, the total body mass of the vehicle only cohort was significantly greater than CBD treated mdx mice and both vehicle and CBD were significantly greater than DFZ treated mice (at week 15, vehicle=31.17 g, CBD=29.42 g, DFX=26.26; 5.6% and 15.8% differences, p<0.05).

Figure 8:
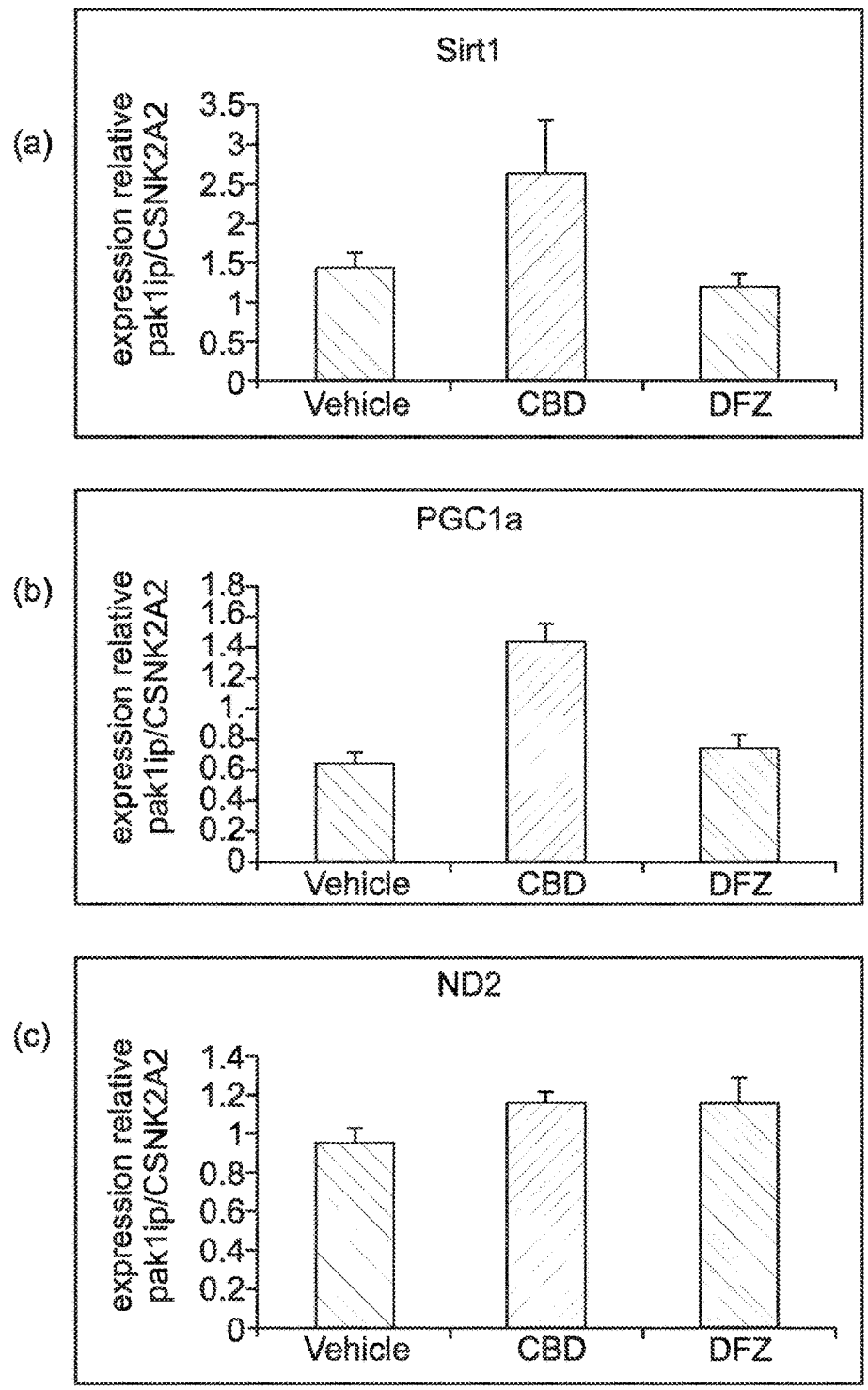
FIG. 8 shows real time PCR expression of DMD gene markers.

FIG. 8 Gastrocnemius muscle were recovered at week 4 and relative gene expressions were determined. (a) Sirtuin-1 (Sirt1) is significantly upregulated in CBD cohort only (84.9%; n=9 p<0.05). (b) PGC1a is significantly upregulated in CBD cohort only (125.8%; n=9 p<0.001). (c) Mitochondrially encoded NADH dehydrogenase 2 (MT-ND2) is significantly upregulated in CBD cohort only (253.2%; n=4 p<0.05).

Figure 9:
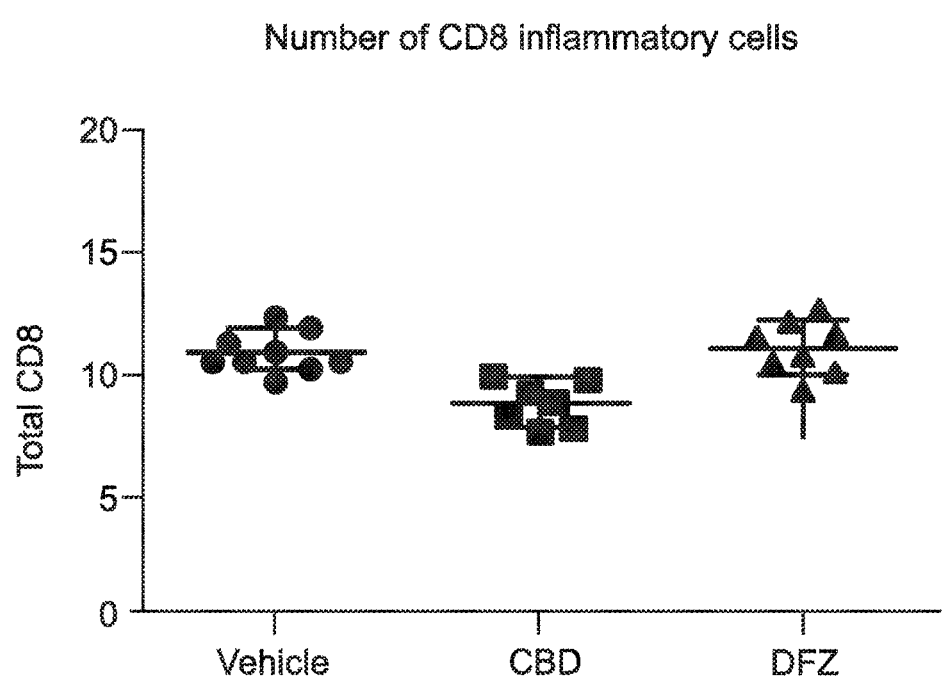
FIG. 9 shows the number of CD8 inflammatory cells.

FIG. 9 Spleens were recovered at week 4 and CD8 positive cells were analysed. The total percentage CD8 population was unaffected by DFZ, however the total percentage CD8 population significantly reduced from 10.9% (vehicle) to 8.7% (CBD); 19.7% difference (n=9; p<0.001).

Definitions

Definitions of some of the terms used to describe the invention are detailed below:

The cannabinoids described in the present application are listed below along with their standard abbreviations.

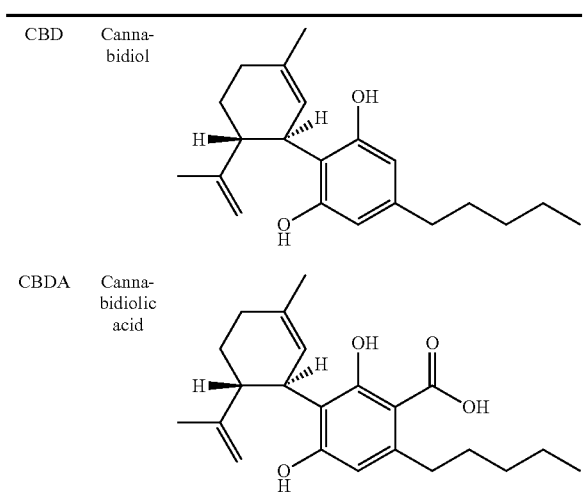

| CBD | Cannabidiol |
| CBDA | Cannabidiolic acid |

-continued

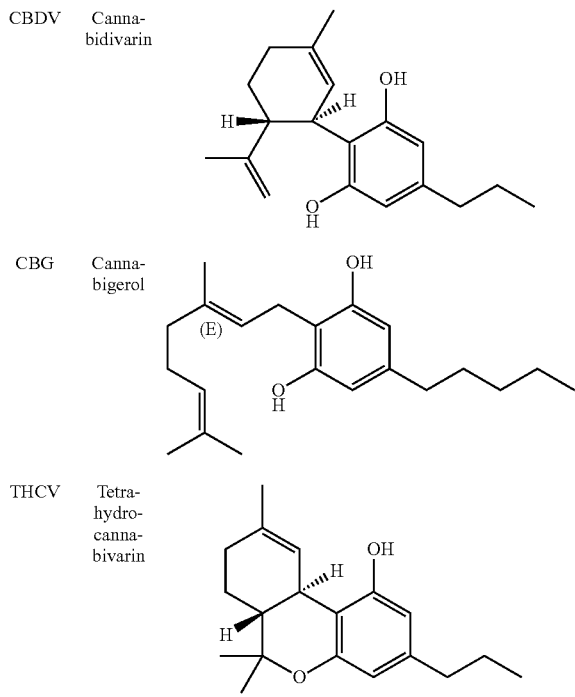

| | |
|---|---|
| CBDV | Cannabidivarin |
| CBG | Cannabigerol |
| THCV | Tetrahydrocannabivarin |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

DETAILED DESCRIPTION

Example 1 below describes the use of the phytocannabinoids CBD, CBDV; CBDA; THCV and CBG in a mouse model of myoblast differentiation.

Example 2 goes on to describe the use of CBD, CBDV and THCV in a model of human satellite cells.

Example 3 describes the use of CBD in an in vivo study in a mammalian model of DMD.

The data presented herein surprisingly demonstrate that the phytocannabinoids CBD, CBDV and THCV, but not CBDA and CBG, may offer a new pharmacological opportunity to treat irreversible degenerative skeletal muscle diseases, such as DMD. Since the former are all able to stimulate differentiation of three different markers.

Example 1: Effect of Phytocannabinoids on Differentiation of Mouse C2C12 Myoblasts Materials and Methods
Cell Culture and Reagents Mouse C2C12 myoblasts were propagated in a growth medium (GM) composed of Dulbecco's modified Eagle's medium supplemented with 10% fetal bovine serum (FBS), 50 U/ml penicillin plus 50 µg/ml streptomycin, and 1% L-glutamine (Invitrogen, Milan, Italy), in a humidified atmosphere of 95% air/5% CO2 at 37° C.

C2C12 is a mouse myoblast cell line. These cells are capable of differentiation and are a useful tool to study the differentiation of myoblast and osteoblast, to express various proteins, and to explore mechanistic pathways.

Exposure of proliferating C2C12 cells for 24 to 72 h to a lower (from 10% to 0.1%) FBS concentration, plus the addition of 5 µg/ml insulin and 5 µg/ml transferrin (differentiation medium, DM), induced their differentiation into myotubes.

Cell Viability

C2C12 cells were seeded at $2 \times 10^3$ cells/cm$^2$ density in 24-well plastic plates. One day after plating, statins (alone or in the presence of phytocannabinoids) was added to the culture medium 24 h. Cell viability was evaluated with the 3-(4,5-dimethylthiazol-2-yl)-2,5-diphenyltetrazolium bromide (MTT; 5 mg/ml; Sigma-Aldrich) reduction assay, and formazan salts formation upon MTT reduction by mitochondria of living cells was detected spectrophotometrically at 595 nm.

Western Blot Analysis

Cells were washed two times in cold PBS and lysed with lysis solution (150 mM NaCl, 1 mM EDTA, pH 7.4, 10 mM Tris-HCl, pH 8, 1% SDS, and protease inhibitors). Lysates (50-60 ug) were boiled 5 min in Laemmli SDS loading buffer and separated by 8% SDS-polyacrylamide gel electrophoresis. Filters were incubated overnight at 4° C. with a mouse anti-MyHC (dilution, 1:1000; Millipore).

An anti-tubulin antibody (dilution, 1:5000; Sigma-Aldrich) was used to check for equal protein loading. Reactive bands were detected by chemiluminescence (ECL-plus; GE Healthcare). Images were analysed on a ChemiDoc station with Quantity one software (Bio-Rad, Segrate, Italy).

mRNA Extraction and Quantitative PCR (qPCR) Analysis

Total RNA was isolated from native tissues by use of the TRI-Reagent (Life Technology, Milan, Italy), reacted with DNase-I (1 U/µl; Sigma-Aldrich) following the manufacturer's instructions, and then quantified by spectrophotometric analysis.

Both sides of the hippocampus were analysed. Final preparation of RNA was considered DNA- and protein-free if the ratio between readings at 260/280 nm was >1.7. The purified mRNA was reverse-transcribed by use of reverse transcriptase (enzyme-VILO) (Life Technology, Milan, Italy). Quantitative real-time PCR was carried out in CFX384 real time PCR detection system (Bio-Rad, Segrate MI, Italy) with specific primers by the use of SYBR Green detection (Bio-Rad, Segrate MI, Italy). Samples were amplified simultaneously in quadruplicate in one-assay run with a nontemplate control blank for each primer pair to control for contamination or primer-dimers formation, and the ct (cycle threshold) value for each experimental group was determined.

The housekeeping genes (the ribosomal protein S16) has been used as an internal control to normalize the ct values, using the 2-dCt formula; differences in mRNA content between groups were as expressed as 2-ddct, as previously described (Iannotti et al. 2013)

Materials

The highly purified phytocannabinoids CBD; CBDV; CBDA; THCV and CBG were tested in this Example.

Statistics

Data are expressed as mean±S.E.M. of the given number of experiments (n). Data sets were compared by use of matched Student's t tests or, if necessary, with one-way analysis of variance, followed by the Newman-Keul test. Statistically significant differences were accepted when p was <0.05.

Results

In order to gain information about the potential effects of phytocannabinoids on myoblast differentiation, C2C12 cells were induced to differentiate for 24-48 h in DM in the presence or absence of various phytocannabinoids.

qPCR analysis was then utilized to evaluated the expression level of the canonical developmentally regulated skeletal markers Myog and Tnnt-1.

As shown in FIG. 1A and FIG. 1B, myoblasts differentiated in the presence of CBDA (1 and 3 µM) or CBG (3 µM) had significantly reduced Myog and Tnnt-1 mRNA expression levels. Whereas, THCV (1 and 3 µM) did not produced significant effects (FIG. 1C).

In contrast, CBD (1 µM) and CBDV (1 and 3 µM) promoted myoblast differentiation, as revealed by the significant increase of Myog and Tnnt-1 mRNA expression (FIG. 2A and FIG. 2B).

The effect of CBD 1 µM on myotube formation was confirmed by western blot analysis. 72 h of cell exposure to DM+1 µM CBD, Myosin Heavy Chain (MyHC) protein expression was significantly increased relative to the control conditions (FIG. 2C).

The potential effect of short term CBD exposure at 1 µM on differentiating C2C12 cells was also tested.

The day after plating, C2C12 myoblasts were exposed to DM in presence or not of 1 µM CBD for 10 min. After this time, DM was refreshed and cells washed before their exposure to DM (without drugs) for the following 3 and 24 hrs. qPCR analysis revealed that after both 3 and 24 h, C2C12 cells exposed to CBD 1 µM had significantly higher transcript levels for both Myog and Tnnt-1 (FIG. 3). These results indicate that a short exposure to CBD is sufficient to promote the myoblast differentiation process.

Conclusions

These data show for the first time that the phytocannabinoids CBD, CBDV, and THCV can regulate skeletal muscle cell differentiation.

In particular the phytocannabinoids CBD and CBDV produced a statistically significant increase in myoblast differentiation (in contrast to the other cannabinoids) as is shown in FIGS. 2A and 2B.

This means these particular phytocannabinoids or combinations thereof may prove to be useful in the treatment or prevention of chronic or degenerative skeletal muscle diseases which are caused by alteration of the differentiation process and subsequent degeneration of skeletal muscle tissue, such as dystrophies, including Duchenne muscular dystrophy.

Example 2: Effect of Phytocannabinoids on Differentiation of Human Satellite Cells Materials and Methods
Cell Culture and Reagents Primary human satellite cells (SC) were purchased from Innoprot Inc (Bizkaia-Spain) and propagated in a growth medium (GM) which contains essential and non-essential amino acids, vitamins, organic and inorganic compounds, hormones, growth factors, trace minerals and a low concentration of fetal bovine serum (5%) (Innoprot lnc/Bizkaia-Spain) in a humidified atmosphere of 95% air/5% $CO_2$ at 37° C.

Exposure of proliferating satellite cells 4-5 days to a lower (from 10% to 0.1%) FBS concentration, plus the addition of 5 µg/ml insulin and 5 µg/ml transferrin (differentiation medium, DM), induced their differentiation into myotubes.

mRNA Extraction and Quantitative PCR (qPCR) Analysis

As described in Example 1

Materials

The highly purified phytocannabinoids CBD; CBDV and THCV were tested in this Example.

Statistics

As described in Example 1.

Results

To further investigate the effects of the cannabinoids CBD, CBDV and THCV on human skeletal muscle precursor cell differentiation qPCR analysis was used.

In particular, skeletal muscle cell differentiation was quantified by measuring the transcript levels of myogenin (Myog), Troponin (Tnnt-1) and Myosin Heavy Chain (MyHC). All of which are widely considered muscle-specific markers, required for myotube formation.

QPCR analysis revealed that after 5 days of SC exposure to differentiation media in the presence of CBD 1 µM, CBDV or THCV 3 µM transcript levels of canonical skeletal muscle differentiation markers such as Myog, Tnnt-1 and MyHC were significantly increased (FIG. 4).

Differentiating primary human satellite cells were also examined in phase contrast mode by means of conventional light microscopy. As shown in FIGS. 5 and 6 respectively, after 4 and 5 days of exposure to DM in presence of CBD 1 µM, CBDV and THCV 3 µM differentiating SC showed clear morphological differences with respect to the control group treated with vehicle (DMSO). In particular, after 5 days of incubation in the presence of phytocannabinoids, the cells appeared more fused and with mature myotubes being larger in size.

This latter difference was more appreciable in cells treated with THCV (FIG. 6).

These effects found in primary human skeletal muscle precursors cells were much more prominent than those observed in mouse C2C12 cells (Example 1).

Conclusions

The data shows that exposure to CBD, CBDV or THCV contributes to an enhanced differentiation of precursor cells into myotubes.

In degenerative skeletal muscle disorders, such as the Duchenne Muscle Dystrophy (DMD), the loss of skeletal muscle precursor (satellite) cells regenerative capacity and the decreased ability to differentiate into mature and functional myotubes lead to progressive muscle weakness with chronic degeneration. It appears that the phytocannabinoids CBD, CBDV, and THCV (in contrast to the cannabinoids CBDA and CBG) are all effective in enhancing differentiation of human skeletal muscle precursor cells and as such should be considered a treatment option for patients with such a condition.

Example 3: Effect of Cannabidiol (CBD) in a Mammalian Model of DMD

Materials and Methods
Animals:

Mdx mice were bred and housed according to Home Office regulations. At 6 weeks of age groups of female mdx mice (control n=18, deflazcort n=18, CBD n=19) were acclimatised to 3.5% Kolliphor/water (v/v) in drinking water.

Control groups were maintained on 3.5% Kolliphor for the duration of the study. Deflazacort (DFZ) groups were maintained on 3.5% Kolliphor for 2 weeks and then maintained on 1.2 mg/kg/day DFZ in 3.5% Kolliphor for 16 weeks (n=8).

CBD groups were acclimatised to 3.5% Kolliphor for 7 days. On day 7, 3.5% Kolliphor was supplemented with CBD at 75 mg/kg/day for 3 days; CBD was then increased to 120 mg/kg/day for 16 weeks (n=8).

Mice and bottles were weighed twice weekly to monitor body mass and consumption. Mice are housed in groups, therefore average consumption is calculated.

Real Time PCR:

Gastrocnemius muscle was recovered at week 4 and relative gene expressions were determined.

RNA was extracted from cells following treatment with CBD. Control RNA was extracted from the control group (RNeasy kit, Qiagen). 2 μg of RNA from each sample was reversed transcribed using oligo dT primers (rt nanoscript 2, Primer Design).

Stable endogenous control genes (Pak1lip1, Htatfs1) were identified using the mouse GeNorm Kit qbase+software (Primer Design).

Real time PCR was conducted using SYBR green (Life Technologies) on an AB Biosystems Thermocycler. All real time PCR experiments were conducted with the following reaction conditions. Initial 95° C. 10 mins, followed by 40 cycles of 95° C. for 15 secs, 60° C. for 1 min, followed by melt curve analysis.

Relative levels of gene expression were determined using the standard curve method and are expressed relative to the average of the endogenous controls.

Inflammatory Markers:

Spleens were recovered at week 4 and CD8 positive cells were analysed.

Results:

FIG. 7 details the body weights of the mice over the 16 weeks of the study. As can be seen the total body mass between vehicle and CBD groups did not differ up to week 4; however deflazacort group was significantly lighter (8.9%, $p<0.05$).

After week 4, the total body mass of the vehicle only cohort was significantly greater than CBD treated mdx mice and both vehicle and CBD were significantly greater than deflazacort treated mice (at week 15, vehicle=31.17 g, CBD=29.42 g, DFX=26.26; 5.6% and 15.8% differences, $p<0.05$).

FIG. 8 details the real time PCR of the gastrocnemius muscle at week 4 and the relative gene expressions. FIG. 8(a) shows that Sirtuin-1 (Sirt1) is significantly upregulated in CBD cohort only (84.9%; n=9 $p<0.05$).

FIG. 8(b) shows that PGC1 a is significantly upregulated in the CBD cohort only (125.8%; n=9 $p<0.001$).

FIG. 8(c) shows that mitochondrially encoded NADH dehydrogenase 2 (MT-ND2) is significantly upregulated in CBD cohort only (253.2%; n=4 $p<0.05$).

FIG. 9 demonstrates the levels of CD8 positive cells in the animal's spleens. It can be seen that the total percentage CD8 population was unaffected by deflazacort, however the total percentage of CD8 population is significantly reduced from 10.9% (vehicle) to 8.7% (CBD); 19.7% difference (n=9; $p<0.001$).

Conclusions:

The in vivo data above demonstrates that CBD is able to treat DMD.

The real time PCR data from the mouse model of DMD demonstrates that all three genes, Sirt-1; PGC1 α; and ND2 were upregulated. These genes are important markers in DMD as follows;

Sirtuin-1 (Sirt-1) is a gene found in humans and other mammals that helps to promote survival by protecting cells during times when food and energy is scarce.

Peroxisome proliferator-activated receptor gamma, coactivator 1 alpha (PGC1α), is a transcriptional co-activator that regulates genes involved in energy metabolism demonstrated for the first time that CBD promotes an oxidative metabolism and angiogenic phenotype in skeletal muscle cells.

Mitochondrially encoded NADH dehydrogenase 2 (MT-ND2) is a gene associated with metabolism.

The statistically significant increase of all these genes in the DMD mice treated with CBD suggests that the CBD is able to promote the up-regulation of genes which will result in an increase in muscle and as such suggests a useful treatment for DMD.

Furthermore the reduction of inflammatory markers with CBD additionally suggests that the treatment is additionally producing an anti-inflammatory effect which will be of use in the treatment of diseases such as DMD.

REFERENCES

Cooper E (2001) A new role for ion channels in myoblast fusion. J Cell Biol 153:F9-F12. Shieh, Neurol Clin. 2013; Muscular dystrophies and other genetic myopathies.; 31(4):1009-29.

Iannotti F A, Barrese V, Formisano L, Miceli F, Taglialatela M (2013) Specification of skeletal muscle differentiation by repressor element-1 silencing transcription factor (REST)-regulated Kv7.4 potassium channels. Mol Biol Cell 24(3):274-284.

Iannotti F A, et al. (2010) Expression, localization, and pharmacological role of Kv7 potassium channels in skeletal muscle proliferation, differentiation, and survival after myotoxic insults. J Pharmacol Exp Ther 332(3):811-820.

The invention claimed is:

1. A method of treating a subject suffering from Duchenne muscular dystrophy (DMD) comprising administering cannabidiol (CBD) to the subject in need thereof, wherein the CBD is highly purified.

2. The method of claim 1, wherein the CBD is administered at a dose between 1 and 1000 mg/kg day.

3. The method of claim 1, wherein the CBD is comprised in a composition comprising one or more excipients.

4. The method of claim 2, wherein the CBD is comprised in a composition comprising one or more excipients.

\* \* \* \* \*